United States Patent [19]

Schulz et al.

[11] Patent Number: 5,059,121
[45] Date of Patent: Oct. 22, 1991

[54] DEVICE AND PROCESS FOR SPRAYING DENTAL MOLDING COMPOUND

[75] Inventors: Hans H. Schulz, Cologne; Horst Jonischkeit, Tuttlingen, both of Fed. Rep. of Germany

[73] Assignee: Bayer Aktiengesellschaft, Leverkusen, Fed. Rep. of Germany

[21] Appl. No.: 566,281

[22] Filed: Aug. 13, 1990

[30] Foreign Application Priority Data

Aug. 25, 1989 [DE] Fed. Rep. of Germany ....... 3928156

[51] Int. Cl.$^5$ ............................................. A61C 3/02
[52] U.S. Cl. ...................................................... 433/88
[58] Field of Search ................................... 433/88, 89

[56] References Cited

U.S. PATENT DOCUMENTS

| 4,540,365 | 9/1985 | Nelson et al. | 433/88 |
| 4,696,644 | 9/1987 | Goof | 433/88 |
| 4,696,645 | 9/1987 | Saupe et al. | 433/88 |
| 4,820,152 | 4/1989 | Warrin et al. | 433/88 |

Primary Examiner—John J. Wilson
Attorney, Agent, or Firm—Sprung Horn Kramer & Woods

[57] ABSTRACT

The device for spraying on a dental impression compound consists of a cylindrical handpiece (1) with a cartridge (5), situated inside it, for the provision of the impression compound, a curved and conically tapering headpiece (3), which can be mounted on the handpiece (1) by means of a bayonet joint or screw joint (2) and has a likewise conically tapering tubular cross-section (4), and a spray nozzle which is arranged on the headpiece (3) and designed as a two-phase nozzle (9, 10, 14). The supply of the impression compound to the spray nozzle takes place by means of an elastic hosepiece (7), at the front (distal) end of which a conical or pyramidal nozzle member (9) is arranged, which has air escape openings (11). At the same time the diameter of the nozzle member (9) must be greater than the smallest diameter of the conical tubular cross-section (4). The length of the elastic hosepiece (7) is dimensioned in such a manner that it is slightly compressed when the headpiece (3) is mounted, so that the nozzle member base (12) is pressed with its external periphery against the conical internal contour (4) of the headpiece (3).

8 Claims, 2 Drawing Sheets

DEVICE AND PROCESS FOR SPRAYING DENTAL MOLDING COMPOUND

The invention relates to a device for spraying on dental impression compounds, consisting of a cylindrical handpiece with a cartridge, situated inside it, for the provision of the impression compound, a curved and conically tapering headpiece, which can be m'ounted on the handpiece by means of a bayonet joint or screw joint and has a likewise conically tapering tubular cross-section, and a spray nozzle which is arranged on the headpiece and designed as a two-fluid nozzle. The invention also relates to a process for spraying on a dental impression compound using this device.

A dental instrument of this type is described in U.S. Pat. No. A-264 305. In this case, the impression compound is delivered from a cartridge into a two-fluid nozzle by means of a pistol-like grip, which displaces a piston in an axial direction, and sprayed by means of compressed air. Compressed air and material delivery can be manipulated separately. The device renders necessary a large number of mechanical construction elements and is assembled in a relatively complicated manner. Cleaning and sterilization are consequently made more difficult. For reasons of economy (lower manufacturing costs), there is also a tendency to fall back upon plastic construction elements which are manufactured by injection moulding, insofar as this does not conflict with work hygiene requirements. As plastic construction elements cannot be sterilized in an autoclave, such parts must be designed with a view to single use.

The aim of the invention is thus to develop an instrument for sprayinq on a viscous dental impression compound, which from an ergonomic point of view is easy to handle, the construction principle and the material selection of which permit low manufacturing costs and which at the same time offers as high a level of work hygiene and safety as is possible.

As already described above, this aim is achieved with an instrument, which consists of a cylindrical handpiece with a cartridge situated inside it, a curved and conical tapering headpiece, which can be mounted on the handpiece and has a likewise conically tapering tubular cross-section, and a spray nozzle which is arranged on the headpiece and designed as a two-phase nozzle. According to the invention, the abovementioned requirements are taken into account in that the supply of the impression compound to the spray nozzle consists of an elastic hosepiece, at the front (distal) end of which a conical or pyramidal nozzle member is arranged, which has air escape openings and the diameter of which is greater than the smallest diameter of the conical tubular cross-section, and in that the length of the elastic hosepiece is dimensioned in such a manner that it is slightly compressed when the headpiece is mounted, so that the nozzle member base is pressed with its external peripherey against the conical internal contour of the headpiece and is thus fixed in the headpiece. The two-phase nozzle is thus formed by the conically tapering tubular cross-section in the headpiece and the conical or pyramidal nozzle member which is gripped inside it, the air (or even another gaseous medium) necessary for operation flowing at great speed through air escape openings between nozzle member and the internal contour of the conically tapering tubular cross-section and subsequently over the surface of the nozzle member. To this end, with the headpiece mounted, the conical tubular cross-section is advantageously connected to an air supply channel in the cylindrical handpiece.

At its rear (proximal) end, the hosepiece is preferably provided with a flange connection which ensures sealing up to the cartridge. This flange constitutes the connection between the hosepiece and the cartridge volume.

The cartridge advantageously has a vent hole which is expediently conducted through the flange connection. This ensures that no sub-pressure can arise in the cartridge during operation of the instrument.

According to a further development, the cartridge with the attached hosepiece consists of a one-piece injection-moulded plastic part.

A further variant of the invention consists in that the hosepiece itself is designed as a cartridge and contains, already pre-packaged, the supply of compound to be delivered which is necessary for the spray treatment.

In this case, the large-volume supply cartridge in the cylindrical handpiece can be dispensed with.

To spray on a dental impression compound, the cartridge is filled with a commercially available dental impression compound. In this connection, however, it is mainly only low-viscosity materials, which form sufficiently fine droplets in the two-phase nozzle and are in this respect physically suitable for a spraying or atomization process, which can be considered.

In particular it is to be avoided that a non-uniform breakaway of the material takes place in the two-phase nozzle and that material accumulations or lumps appear in the spray jet.

It has become apparent that this disadvantage can be avoided if, according to a preferred embodiment of the invention, a low-viscosity, addition-crosslinking silicone impression compound, in which the silicone components are extensively freed of volatile ingredients by evaporation and in which precipitated or pyrogenically prepared silicic acid is incorporated into vinyl-terminated polysiloxanes, is used as a dental impression compound. Even thin, sprayed on films of a impression material of this composition have a high tensile strength and elongation at tear. Furthermore, dimensional changes upon cross-linking of the material, e.g. shrinkages, are minimized.

With the invention, the following advantages are achieved:

The spraying instrument consists cf a maximum five construction elements and can be manufactured economically. In the variants, in which the hosepiece and the cartridge form an inteqrated construction element or the hosepiece itself serves as a cartridge, only three construction elements are in fact required.

Insofar as headpiece and handpiece are made of metal, the instrument can conveniently be sterilized in an autoclave. To this end, the hosepiece with the nozzle member and possibly the flange connection are intended only for single use, that is to say for each treatment of a patient, a new hosepiece is inserted into the headpiece.

The device is of relatively low weight and offers ergonomically good handling. For supply with compressed air, the device is ccnnected, via an appropriate connection at its rear (proximal) end, to a compressed air source with foot switch as is anyway available in dental practice.

The material flow from the cartridge into the two-phase nozzle takes place solely as a result of the ejector effect on the two-phase nozzle, that is to say in the two-phase nozzle, the impression compound is drawn out of the cartridge through the hosepiece. In previously known impression compound spraying devices or syringes, the material had to be extruded towards the nozzle by means of a piston displaceable in the cartridge.

With the use of low-viscosity, addition-crosslinking silicone impression compounds, in which the volatile ingredients of the silicone components have been reduced and to which a silicone/silicic acid compound has been added, very fine and uniform spray films can be formed, with minimal dimensional changes and good resistances to tearing, which is a prerequisite for perfect adaptation of the material to the hard tooth substance.

An exemplary embodiment of the invention is described in greater detail below.

Figure 1:
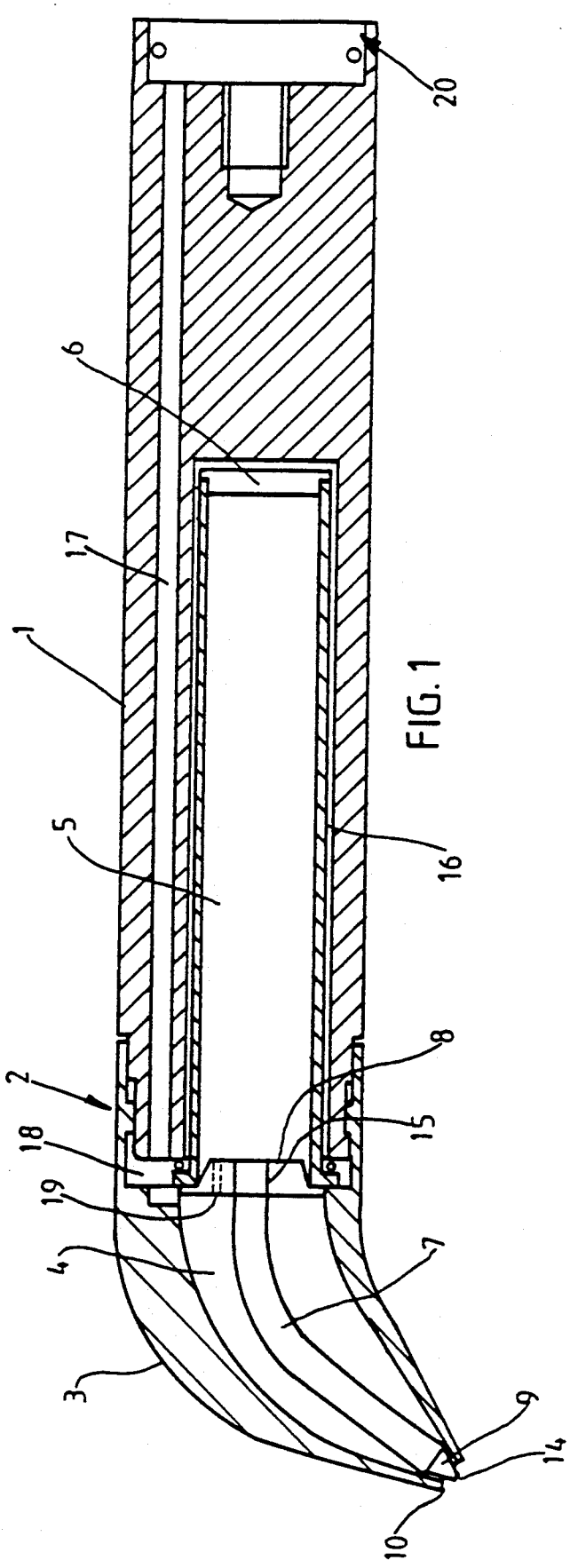
FIG. 1 shows a longitudinal section through the spraying instrument.

According to FIG. 1, a conically tapering, curved or angled headpiece 3, which has a likewise conically tapering tubular cross-section 4, is mounted on a cylindrical handpiece 1 by means of a bayonet joint 2. Inside the handpiece 1, there is a chamber 16 to accommodate a cartridge 5 which is filled with a dental impression compound. The cartridge 5 is provided at its rear (proximal) end with a cover plate 6. At the front (distal) end of the cartridge 5, an elastic hosepiece 7 is flanged on flange connection 8. The hosepiece 7 has at its front (distal) end a nozzle member 9 which, together with the mouth 10 of the headpiece 3, forms a two-phase or two-fluid nozzle. Within the concept of the present invention one phase is the compressed air, whereas the other phase is the material to be sprayed. The nozzle member 9 is in the form of a truncated cone or pyramid, the cross-sectional area tapering towards the outside (see also FIG. 2).

Figure 2:
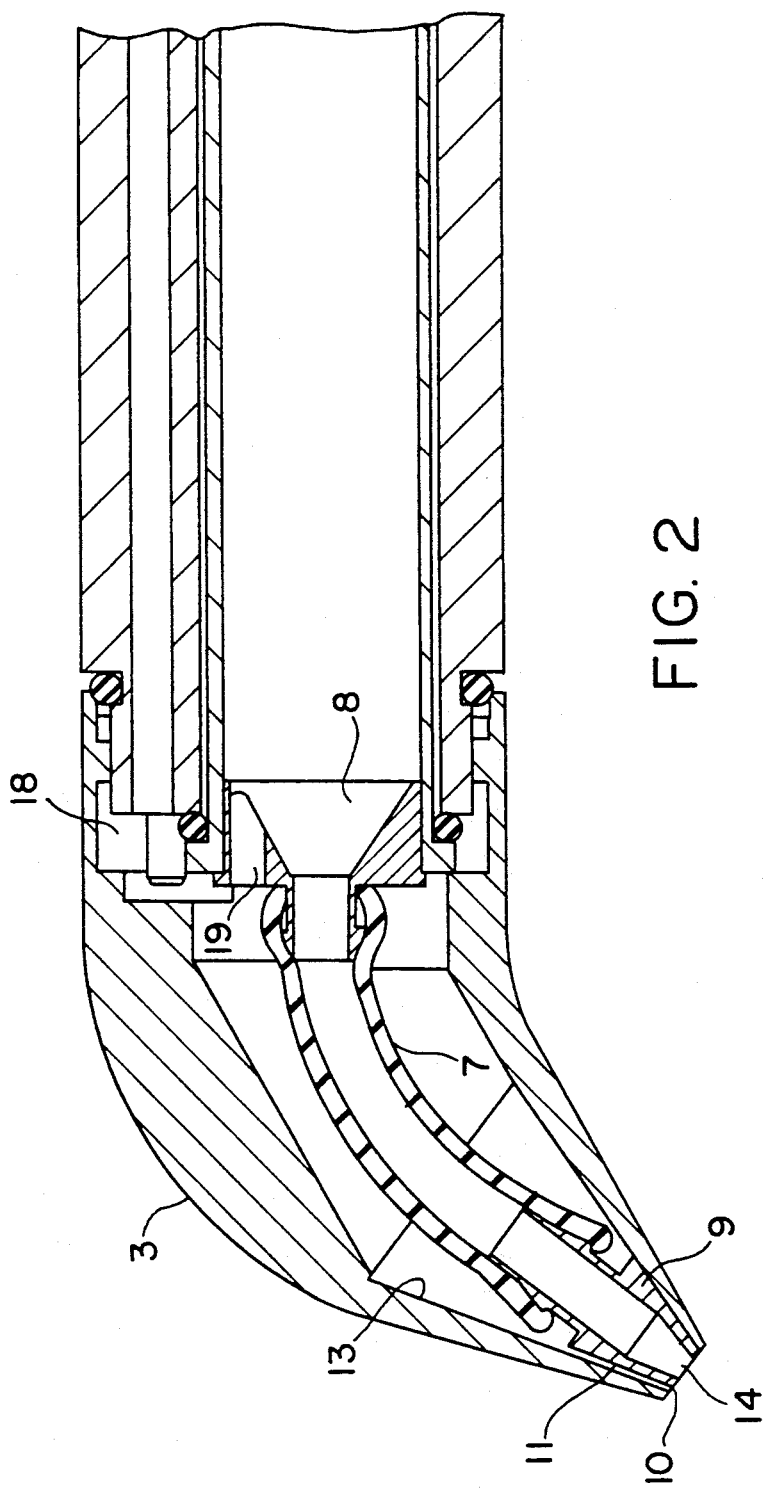
FIG. 2 shows the headpiece of the instrument with the associated two-fluid nozzle.

As can be seen from FIG. 2, air escape channels 11 are, in the case of a conical profile, milled into the nozzle member 9, distributed uniformly over the surface area. In the case of a pyramidal cross-section of the nozzle member 9, segment-shaped air escape openings (11) remain between the periphery of the nozzle member base 12 and the internal contour 13 of the headpiece 3. In both cases, the compressed air, which is supplied to the tubular cross-section 4, flows through the air escape openings 11 via the surface of the nozzle member 9 to the nozzle opening 14.

With the headpiece 3 mounted, the conically designed flange 8 is pressed against the cartridge 5, so that a sealing connection of the hosepiece 7 to the cartridge volume is ensured. The impression material situated in the cartridge 5 can enter into the hosepiece 7 through a drilling 15 in the flange 8.

The hosepiece 7 consists of an elastic material and its length is dimensioned in such a manner that it is slightly compressed when the headpiece is mounted. The length of the hosepiece 7 is thus slightly greater (5% to 10%) than the shortest connection between the supporting point of the nozzle member 9 on the internal contour 13 of the headpiece and the mouth of the drilling 15 in the flange 8 at the other end. As a result of the elastic restoring force which counteracts arching of the hosepiece 7, the nozzle member base 12 is pressed with its external periphery against the conical internal contour 13 of the headpiece 3, as a result of which the nozzle member 9 is fixed in the conically tapering tubular cross-section 4. is a prerequisite for this that the diameter of the nozzle member base 12 is greater than the mouth cross-section of the headpiece 3 at the front end and that the taper (conicity) of the nozzle member 9 corresponds to the taper of the conically tapering tubular cross-section 4 the mouth cross-section 10 (see FIG. 2). At the same time, in this connection, a reproducible, accurately fitting centring of the nozzle member 9 in the tubular cross-section takes place. In practice, the dimensions are selected in such a manner that the nozzle opening 14 lies approximately in the same plane as the mouth cross-section 10 of the headpiece 3.

As a result of the suction effect of the air which flows over the nozzle member surface, the ixpression material situated in the hosepiece 7 is drawn off and emerges at the nozzle openinq 14. Here it is caught by the air flow and divided up into small droplets (spray effect). The necessary compressed air gains access to the conical tubular cross-section 4 through an air supply channel 17 in the handpiece 1 and an opening 18. In order to prevent low pressure, which would hinder the continued flow of the material, building up when material leaves the cartridge 5, a vent hole 19 is arranged in the flange 8.

The hosepiece 7, together with the nozzle member 9 is expediently manufactured on the flange 8 as an injection-moulded part from a suitable thermoplastic, e.g. polycarbonate. Manufacturing costs are consequently so low that only a single use is to be considered for this construction element, that is to say the hosepiece 7 is designed with the nozzle member 9 and the flange 8 as a disposable construction element.

Acccording to an alternative embodiment, the cartridge 5 can also be manufactured together with the hosepiece 7 and the nozzle member 9 as a one-piece integrated injection-moulded plastic part. A further reduction in production and material costs is possible if the cartridge 5 is dispensed with completely and the hosepiece 7 is instead used as the sole storage volume for the impression compound. The flange 8 or a similar attachment then serves only to support the hosepiece 7 in the handpiece 1 when the headpiece 3 is mounted. This variant presents itself when the instrument is used relatively infrequently and only very small quantities of impression material are required.

To operate the instrument, the handpiece 1 is connected to a compressed air hose by means of a commercially available plug-in connector 20. At the same time the connection of the air supply channel 17 to the compressed air source is made. The air supply channel 17 is designed in this case in the form of a long, axially parallel bore through the housing wall of the handpiece 1 Instead of this long bore the air supply can also take place through the annular passage surrounding the cartridge 5. In this case, the annular space around the cartridge 5 must be slightly larger. If necessary, additional measures must be taken for support of the cartridge 5 in the handpiece 1.

A typical impression process using the new spraying instrument takes place in the following manner:

(a) Preparation of the area for which an impression is to be made and selection of a suitable impression tray.

(b) Filling the impression compound into the cartridge 5.

(c) Introduction of the cartridge 5 into the handpiece 1.

(d) Insertion of the hosepiece 7 with the associated flange 8 into the cartridge 5.

(e) Fitting the headpiece 3 over the hosepiece 7 and locking of the headpiece 3 on the handpiece 1 by means of a bayonet joint 2, the hosepiece 7 pushing with the nozzle member 9 towards the mouth 10 of the tubular piece 3 and securing itself firmly there; also fixing the flange 8 to the cartridge 5.

(f) Connection of the instrument to a compressed air source by means of the plug-in connector 20.

(g) Spraying of a thin layer of impression compound onto the area of the hard tooth subs&ance and mucous membrane for which an impression is to be made by means of a foot switch.

(h) Filling further impression compound into the impression tray and positioning of impression tray for impression proper.

It has been found that, from the large number of known compositions of impression materials for a self-priming spraying process as described above, very low-viscosity, addition-crosslinking silicone impression compounds, are particularly suitable. By means of the use of silicone components, in which the volatile ingredients are reduced to a maximum of 1.5%, preferably 0.8%, by means of thin-film evaporators or falling-film evaporators, very low dimensional change values are obtained. This is described in greater detail in EP 0,162.211.

On the other hand, by means of the use of a silicone-silicic acid compound, as described in DE 34 23 823, the resistance to tearing of the impression compounds, which are produced from low-viscosity silicone components, can be improved, without the viscosity of the impression compounds being significantly increased.

The handpiece 1 and the headpiece 3 are expediently made of metal. The cartridge 5 can consist of metal or plastic. The hosepiece 7 with the nozzle member 9 and the flange 8 is designed for single use and consists of a thermoplastic, e.g. polycarbonate, which also ensures the necessary elasticity of the hosepiece 7. When cartridge 5 and hosepiece 7 have been removed, the instrument can be conveniently sterilized in an autoclave.

We claim:

1. Device for spraying on dental impression compounds, comprising a cylindrical handpiece (1) being capable of storing a cartridge (5) therein for the provision of the impression compound, a curved and conically tapering headpiece (3), which can be mounted on the handpiece (1) by means of a bayonet joint or screw joint (2) the headpiece having a likewise conically tapering internal contour and a spray nozzle (9, 10, 14) which is provided with a supply tube for delivery of the impression compound the said supply tube for delivery of the impression compound consisting of an elastic hosepiece (7), the front (distal) end of which is provided with a conical or pyramidal nozzle member (9) which has air escape openings (11) and the diameter of which is greater than the smallest diameter of the conical tubular cross-section (4), and wherein the length of the elastic hosepiece (7) is dimensioned in such a manner that it is slightly compressed when the headpiece (3) is mounted, so that the nozzle member base (12) is pressed with its external periphery against the conical internal contour (4) of the headpiece (3).

2. Device according to claim 1 characterized in that, with the headpiece (3) mounted, the conical tubular cross-section (4) is connected to an air supply channel (17) in the handpiece (1).

3. Device according to claim 1, characterized in that, at its rear (proximal) end, the hosepiece (7) is provided with a flange connection (8) which ensures sealing up to the cartridge (5).

4. Device according to claim 1, characterized in that the cartridge (5) has a vent hole (19).

5. Device according to claim 4, characterized in that the vent hole (19) is conducted through the flange connection (8).

6. Device according to claim 1, characterized in that the cartridge (5) with the attached hosepiece (7) is a one-piece injection-moulded plastic part.

7. Device according to claim 1, characterized in that the hosepiece (7) itself forms a cartridge containing the dental impression compound.

8. Process for spraying on a dental impression compound using the device comprising a cylindrical handpiece (1) being capable of storing a cartridge (5) therein for the provision of the impression compound, a curved and conically tapering headpiece (3), which can be mounted on the headpiece (1) by means of a bayonet joint or screw joint (2) the headpiece having a likewise conically tapering internal contour and a spray nozzle (9, 10 ,14) which is provided with a supply tube for delivery of the impression compound the said supply tube for delivery of the impression compound consisting of an elastic hosepiece (7), the front (distal) end of which is provided with a conical or pyramidal nozzle member (9) which has air escape openings (11) and the diameter of which is greater than the smallest diameter of the concial tubular cross-section (4), and wherein the length of the elastic hosepiece (7) is dimensioned in such a manner that it is slightly compressed when the headpiece (3) is mounted, so that the nozzle member base (12) is pressed with its external periphery against the conical internal contour (4) of the headpiece (3) characterized in that a low-viscosity, addition-crosslinking silicone impression compound, in which the silicone components are extensively freed of volatile ingredients by evaporation and in which precipitated or pyrogenically prepared silicic acid is incorporated into vinyl-terminated polysiloxanes, is used as a dental impression compound.

* * * * *